(12) United States Patent
Oka et al.

(10) Patent No.: US 7,251,035 B2
(45) Date of Patent: Jul. 31, 2007

(54) OPTICAL CELL MEASUREMENT APPARATUS

(75) Inventors: Koichi Oka, Otsu (JP); Satoshi Nitta, Kameoka (JP)

(73) Assignee: Otsuka Electronics Co., Ltd., Osaka (JP)

( * ) Notice: Subject to any disclaimer, the term of this patent is extended or adjusted under 35 U.S.C. 154(b) by 44 days.

(21) Appl. No.: 11/134,296

(22) Filed: May 23, 2005

(65) Prior Publication Data

US 2005/0280825 A1   Dec. 22, 2005

(30) Foreign Application Priority Data

Jun. 17, 2004   (JP) ............................. 2004-180256

(51) Int. Cl.
*G01N 21/00*   (2006.01)
(52) U.S. Cl. ....................... 356/437; 356/246
(58) Field of Classification Search ................ 356/437
See application file for complete search history.

(56) References Cited

U.S. PATENT DOCUMENTS

| | | | | |
|---|---|---|---|---|
| 4,547,675 A | * | 10/1985 | Muggli et al. | 356/438 |
| 4,953,976 A | * | 9/1990 | Adler-Golden et al. | 356/301 |
| 5,068,798 A | * | 11/1991 | Heath et al. | 356/437 |
| 5,726,752 A | * | 3/1998 | Uno et al. | 356/246 |
| 6,339,472 B1 | * | 1/2002 | Hafeman et al. | 356/436 |
| 6,356,700 B1 | * | 3/2002 | Strobl | 385/147 |

FOREIGN PATENT DOCUMENTS

| | | |
|---|---|---|
| EP | 0 497 434 A3 | 8/1992 |
| GB | 868357 | 5/1961 |
| JP | 05-322747 | 12/1993 |
| JP | 2000-35363 | 2/2000 |
| RU | 2 178 875 C2 | 1/1998 |
| WO | WO 01/13091 A2 | 2/2001 |

\* cited by examiner

*Primary Examiner*—Layla G. Lauchman
*Assistant Examiner*—Juan D. Valentin, II
(74) *Attorney, Agent, or Firm*—Finnegan, Henderson, Farabow, Garrett & Dunner, L.L.P.

(57) ABSTRACT

An inventive optical cell measurement apparatus comprises a light source (S) which emits light having a predetermined wavelength range, a first mirror (M1) which reflects the light emitted from the light source (S), a long light path gas cell (1) to which the light reflected on the first mirror (M1) is introduced, a second mirror (M2) which reflects light outputted from the long light path gas cell (1), a sensor (D) which detects the light reflected on the second mirror (M2), and optical elements (21, 22) disposed in a light path extending from the light source (S) to the sensor (D) and each having a bifocal property with different focal lengths as measured in two directions (X, Y) perpendicular to the light path. With this arrangement, the aberration of spherical mirrors (6, 7) disposed in the gas cell (1) is corrected, thereby preventing reduction of the transmittance of the gas cell (1).

4 Claims, 4 Drawing Sheets

OPTICAL CELL MEASUREMENT APPARATUS

BACKGROUND OF THE INVENTION

1. Field of the Invention

The present invention relates to an optical cell measurement apparatus for measuring spectrum of a substance present in a gas cell.

2. Description of Related Art

For measurement of a spectrum, a plurality of spherical mirrors are disposed in opposed relation in a gas cell, and light is inputted obliquely into the cell thereby to be reflected on the spherical mirrors a plurality of times (twice to 20 times) and then outputted. Thus, the length of a light path is substantially extended. The gas cell having the substantially extended light path is generally referred to as "long light path gas cell." A measurement method using the long light path gas cell makes it possible to convert a low level spectrum which is generally difficult to measure into a relatively strong signal for measurement of the spectrum (W001/013091).

With the long light path gas cell, however, it is necessary to employ the spherical mirrors and input the light not squarely but obliquely with respect to the spherical mirror in the gas cell. Therefore, a focus position at which vertically polarized light rays are brought to a focus does not coincide with a focus position at which horizontally polarized light rays are brought to a focus due to aberration of the spherical mirror. This tendency is increased as the angle of the obliquely inputted light increases. That is, the tendency becomes more remarkable as a distance between a light input position and a light output position of the gas cell increases.

Therefore, if the light rays polarized in one of the polarization directions are brought to a focus for outputting the light rays inputted into the gas cell, the light rays polarized in the other polarization direction are brought out of a focus. This makes it impossible to output all the light rays, resulting in reduction of the transmittance of the gas cell.

It is therefore an object of the present invention to provide an optical cell measurement apparatus which has a function of correcting the aberration of a spherical mirror disposed in a gas cell thereof to prevent reduction of the transmittance of the gas cell.

SUMMARY OF THE INVENTION

An optical cell measurement apparatus according to the present invention comprises a light source which emits light having a predetermined wavelength range, a first mirror which reflects the light emitted from the light source, a long light path gas cell to which the light reflected on the first mirror is introduced, a second mirror which reflects light outputted from the long light path gas cell, a sensor which detects the light reflected on the second mirror, and an optical element disposed in a light path extending from the light source to the sensor and having a bifocal property with different focal lengths as measured in two directions perpendicular to the light path.

The first mirror and the second mirror may each double as the bifocal optical element, or may each be mounted with the bifocal optical element.

With this inventive arrangement, the bifocal optical element is inserted in the optical path between the light source and the sensor, whereby light rays inputted in the long light path gas cell in the two directions perpendicular to the light path are brought to a focus at substantially the same position. Further, light rays outputted in the two directions perpendicular to the light path from the long light path gas cell are brought to a focus at substantially the same position. Therefore, all the light rays are inputted into the long light path gas cell and outputted from the long light path gas cell irrespective of a polarization direction. As a result, a spectrum can be measured with a higher level of sensitivity without reduction of the transmittance of the gas cell.

Since the aberration is corrected, a distance between a light inlet position and a light outlet position of the gas cell can be increased. This makes it easier to provide a short light path gas cell between the light inlet position and the light outlet position. More specifically, the optical cell measurement apparatus according to the present invention may further comprise movement means which moves the first mirror and the second mirror from the light path between the light source and the sensor, and a short light path gas cell disposed between the light source and the sensor in the light path from which the first mirror and the second mirror are retracted. With this arrangement, the provision of the movement means makes it possible to selectively use the long light path gas cell and the short light path gas cell for the measurement.

The foregoing and other advantages, features and effects of the present invention will become more apparent from the following detailed description of the preferred embodiments with reference to the attached drawings.

DETAILED DESCRIPTION OF PREFERRED EMBODIMENTS

Figure 1:
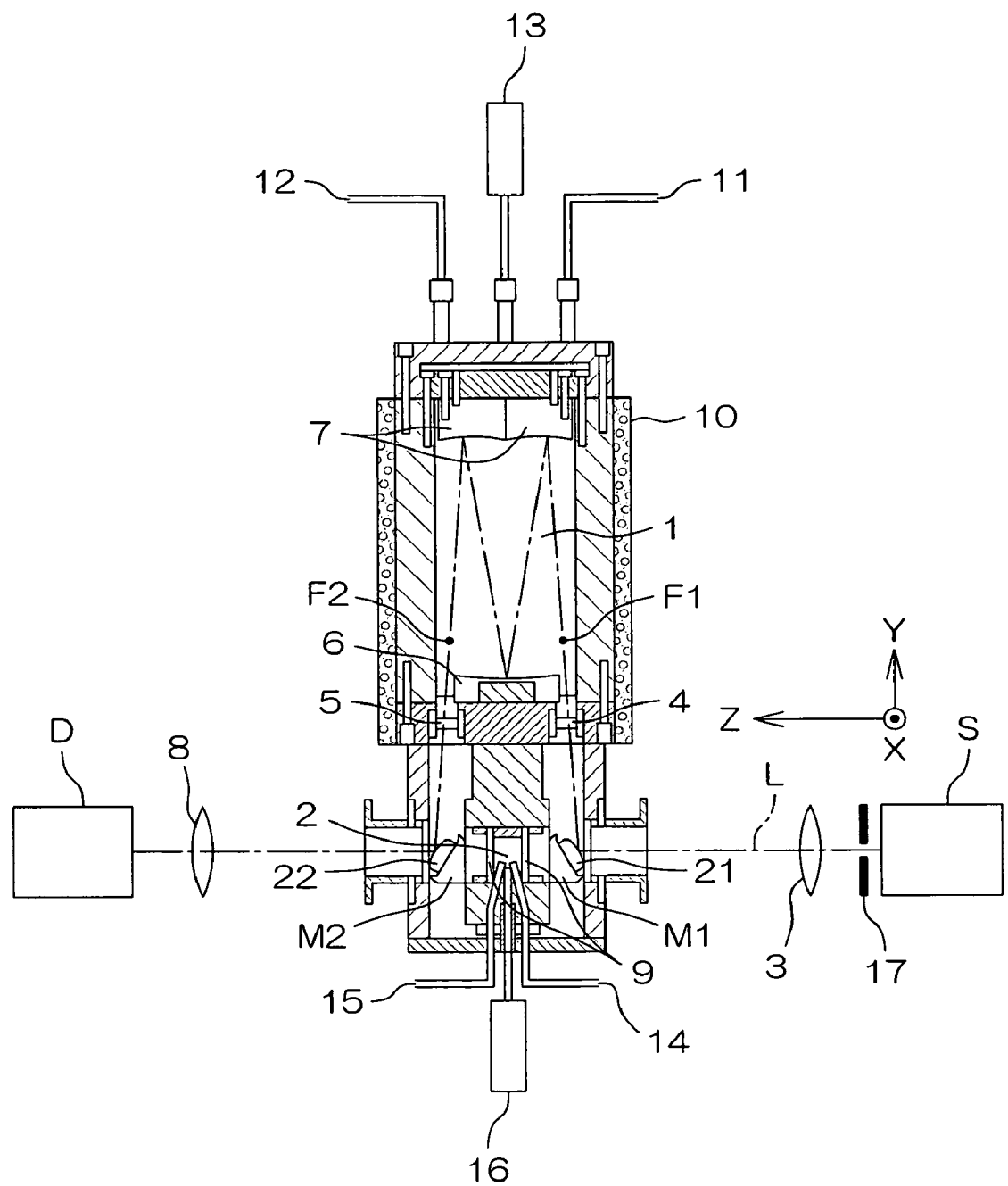
FIG. 1 is a sectional view of an inventive optical cell measurement apparatus including two gas cells, i.e., a long light path gas cell and a short light path gas cell.

FIG. 1 is a sectional view of an inventive optical cell measurement apparatus including two gas cells, i.e., a long light path gas cell 1 and a short light path gas cell 2.

The optical cell measurement apparatus includes a light source S, a slit 17, a lens 3 which converges light emitted from the light sources, and a movable mirror M1 which reflects the light converged by the lens 3 to apply the light to the long light path gas cell 1 through a gas cell window 4.

The light source S is, for example, an SiC lamp. The SiC lamp has a broad-band infrared spectrum ranging from 400 $cm^{-1}$ to 7000 $cm^{-1}$. This range is converted into a wavelength range of 1429 nm to 25000 nm by the following conversion equation:

$$10^7/X(nm) = Y(cm^{-1})$$

wherein X is a wavelength and Y is a wave number.

The light applied to the long light path gas cell 1 through the gas cell window 4 is reflected on objective mirrors 7 and a condenser mirror 6 provided in the long light path gas cell 1 a plurality of times, and outputted through a gas cell window 5. The objective mirrors 7 and the condenser mirror 6 are each prepared, for example, by vapor-depositing gold on a stainless concave mirror.

The light outputted through the gas cell window 5 is reflected on a movable mirror M2, and inputted to a detector D through a condenser lens 8. The gas cell windows 4, 5 are each composed of, for example, ZnSe.

The long light path gas cell 1 has a gas inlet 11 through which a gas to be subjected to wavelength spectrum measurement is introduced into the gas cell 1, and a gas outlet 12 through which the introduced gas is discharged out of the gas cell 1. A pressure transducer 13 which measures the inside pressure of the long light path gas cell 1 is attached to the gas cell 1. A reference numeral 10 denotes a heat insulating material provided around the long light path gas cell 1.

The short light path gas cell 2 is disposed in a light path L extending linearly from the light source S to the detector D through the lenses 3, 8. Light applied to the short light path gas cell 2 through a gas cell window 9 passes through the inside of the short light path gas cell 2, and is outputted through another gas cell window 9. The gas cell windows 9 are each composed of, for example, ZnSe.

The short light path gas cell 2 has a gas inlet 14 through which a gas to be subjected to wavelength spectrum measurement is introduced into the gas cell 2, and a gas outlet 15 through which the introduced gas is discharged out of the gas cell 2. A pressure transducer 16 which measures the inside pressure of the short light path gas cell 2 is attached to the gas cell 2.

The movable mirror M1, M2 are each prepared, for example, by vapor-depositing gold on a quartz plate.

In FIG. 1, the light path L along which the light is propagated extends along a Z-axis, and an X-axis and a Y-axis extend perpendicularly to the Z-axis.

In the present invention, bifocal lenses 21, 22 each having different focal lengths as measured along the X-axis and the Y-axis perpendicular to the light path L are respectively attached to surfaces of the movable mirrors M1, M2. The bifocal lenses 21, 22 are preferably composed of a material which transmits the light of the spectral wavelength range emitted from the light source S. The material for the bifocal lenses 21, 22 is, for example, Zinc Selenide (ZnSe), Barium Fluoride ($BaF_2$), or Cesium Iodide (CsI).

Figure 2:
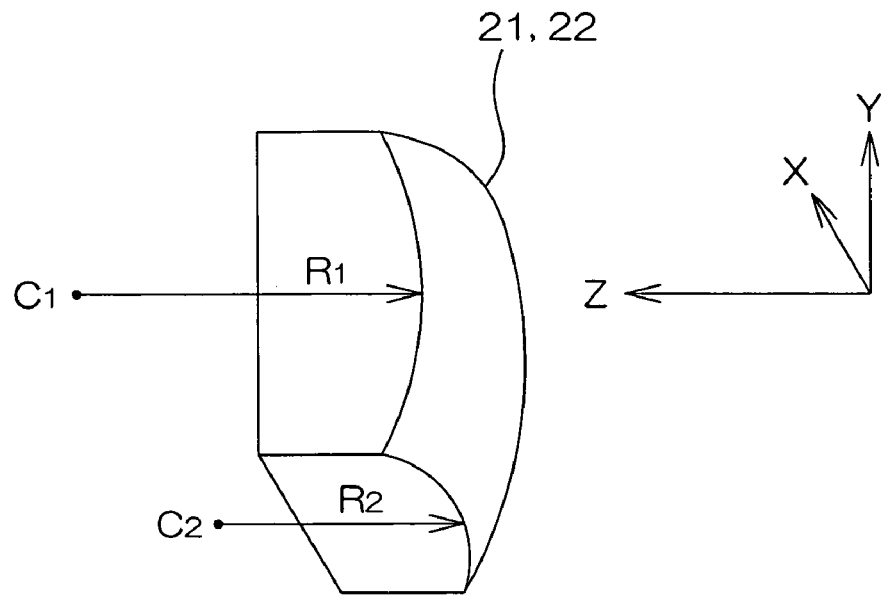
FIG. 2 is a perspective view illustrating the shape of an exemplary bifocal lens.

The shape of each of the bifocal lenses 21, 22 is shown in FIG. 2.

The curved surfaces of the bifocal lenses 21, 22 each have a curvature in a YZ-plane and a curvature in an XZ-plane. The center of the curvature in the YZ-plane and the center of the curvature in the XZ-plane are denoted by C1 and C2, respectively. Further, the radius of the curvature in the YZ-plane and the radius of the curvature in the XZ-plane are indicated by R1 and R2, respectively.

The curvature radii R1, R2 of the bifocal lenses 21, 22 are properly adjusted so that a focus position at which light rays polarized along the X-axis are brought to a focus coincides with a focus position at which light rays polarized along the Y-axis are brought to a focus. The focus positions thus degenerated on a light input side and on a light output side of the long light path gas cell 1 are indicated by reference characters F1 and F2, respectively, in FIG. 1.

Biconvex lenses with R1>0, R2>0 are shown in FIG. 2, but the bifocal lenses 21, 22 are not limited to the biconvex lenses. Concave-convex lenses with R1<0, R2>0 or with R1>0, R2<0 or biconcave lenses with R1<0, R2<0 may be used depending on the positions F1, F2.

Figure 3:
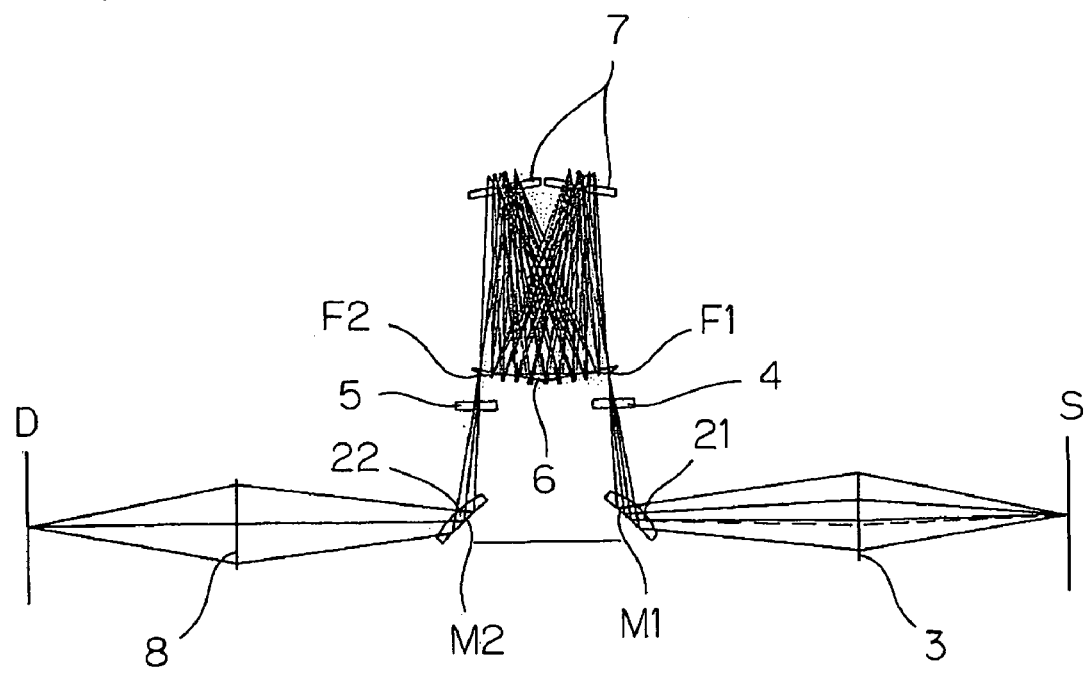
FIG. 3 is a light path diagram of the inventive optical cell measurement apparatus in which bifocal lenses are inserted in a light path.

FIG. 3 is a light path diagram in which the bifocal lenses 21, 22 are inserted in the light path. The light source S is positioned at a right end of FIG. 3. Light rays emitted from the light source S are converged by the lens 3, and reflected on the movable mirror M1 generally perpendicularly. Then, the reflected light rays are inputted into the gas cell 1 through the gas cell window 4. At this time, the astigmatism is corrected by the bifocal lens 21 attached to the movable mirror M1, so that the light rays are converged on the focus position F1 irrespective of the polarization direction. In the gas cell 1, the light rays are reflected on the objective mirrors 7 and the condenser mirror 6 a plurality of times, and converged on the focus position F2 which is in conjugate relation to the focus position F1. The light rays converged on the focus position F2 are outputted from the gas cell 1 through the gas cell window 5, and reflected generally perpendicularly on the movable mirror M2. At this time, the astigmatism is corrected by the bifocal lens 22 attached to the movable mirror M2. The light rays reflected generally perpendicularly on the movable mirror M2 are converged on a light receiving surface of the sensor D through the lens 8.

As described above, the light rays are converged on the focus positions F1, F2 by the bifocal lenses 21, 22 respectively attached to the movable mirrors M1, M2 irrespective of the polarization direction, so that the light rays can efficiently be inputted into and outputted from the gas cell 1. Therefore, the transmittance of the gas cell can be maintained at a higher level, thereby achieving the spectrum measurement with a higher level of sensitivity.

Figure 4:
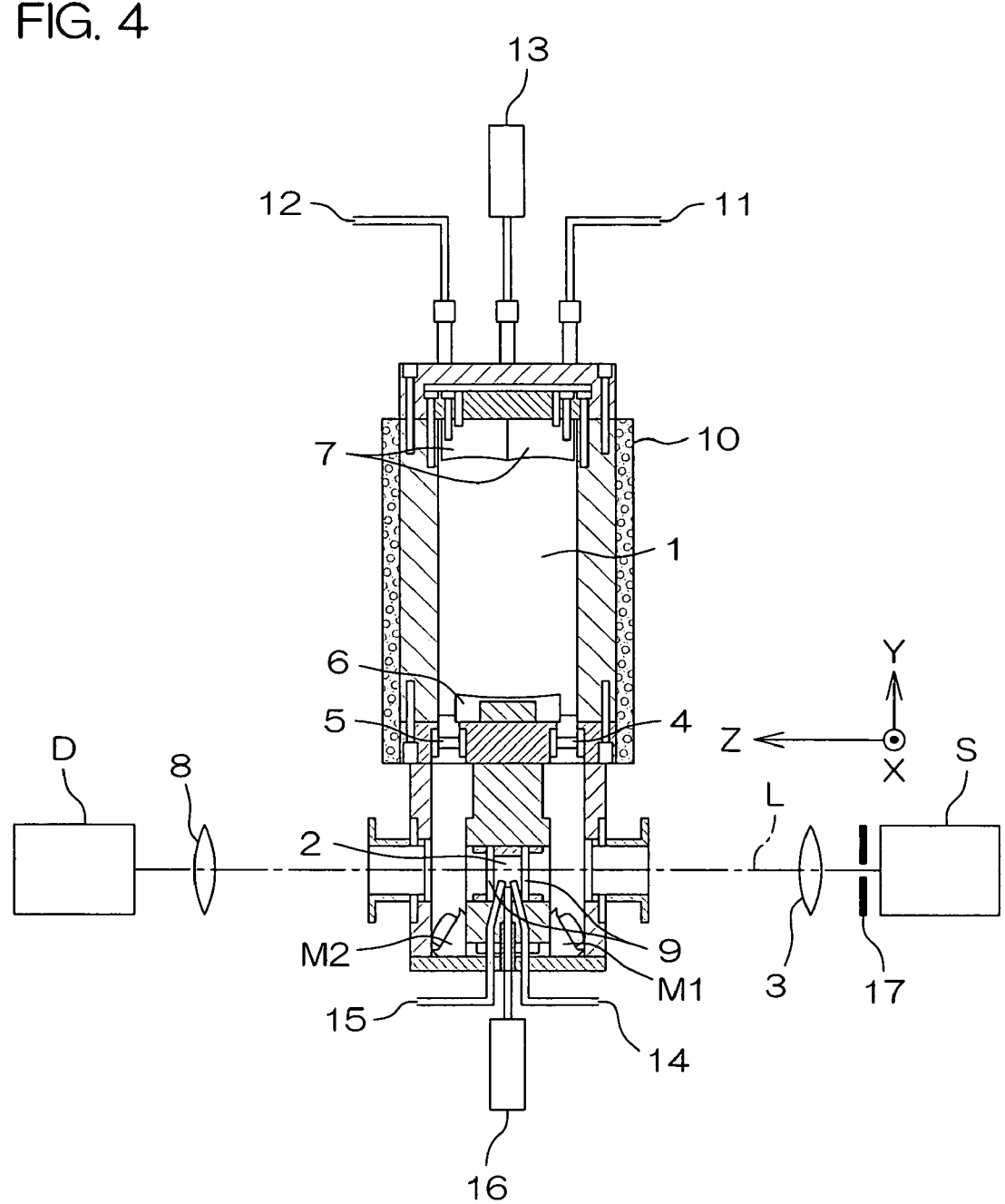
FIG. 4 is a sectional view illustrating a state of the inventive optical cell measurement apparatus in which movable mirrors M1, M2 are retracted from the light path.

FIG. 4 is a sectional view illustrating a state of the inventive optical cell measurement apparatus in which the movable mirrors M1, M2 are retracted from the light path L.

The movable mirrors M1, M2 are thus moved, making it possible to perform measurement on a gas contained in the short light path gas cell 2.

Movement means for moving the movable mirrors M1, M2 may have any of various conceivable constructions. For example, (1) the movable mirrors M1, M2 may be moved vertically (along the Y-axis in FIG. 4) as shown in FIG. 4, or moved horizontally (along the X-axis in FIG. 4). In this case, a combination of a driving shaft and an actuator or a combination of a ball screw and a motor may be used as a driving mechanism for the movement of the movable mirrors M1, M2. The movable mirrors M1, M2 are mechanically moved either automatically or manually. Alternatively, (2) the movable mirrors M1, M2 may be rotated about an axis (e.g., the Z-axis) for the movement. In this case, a rotation actuator or a rotation solenoid may be used as a driving mechanism for the movement of the movable mirrors M1, M2.

Figure 5:
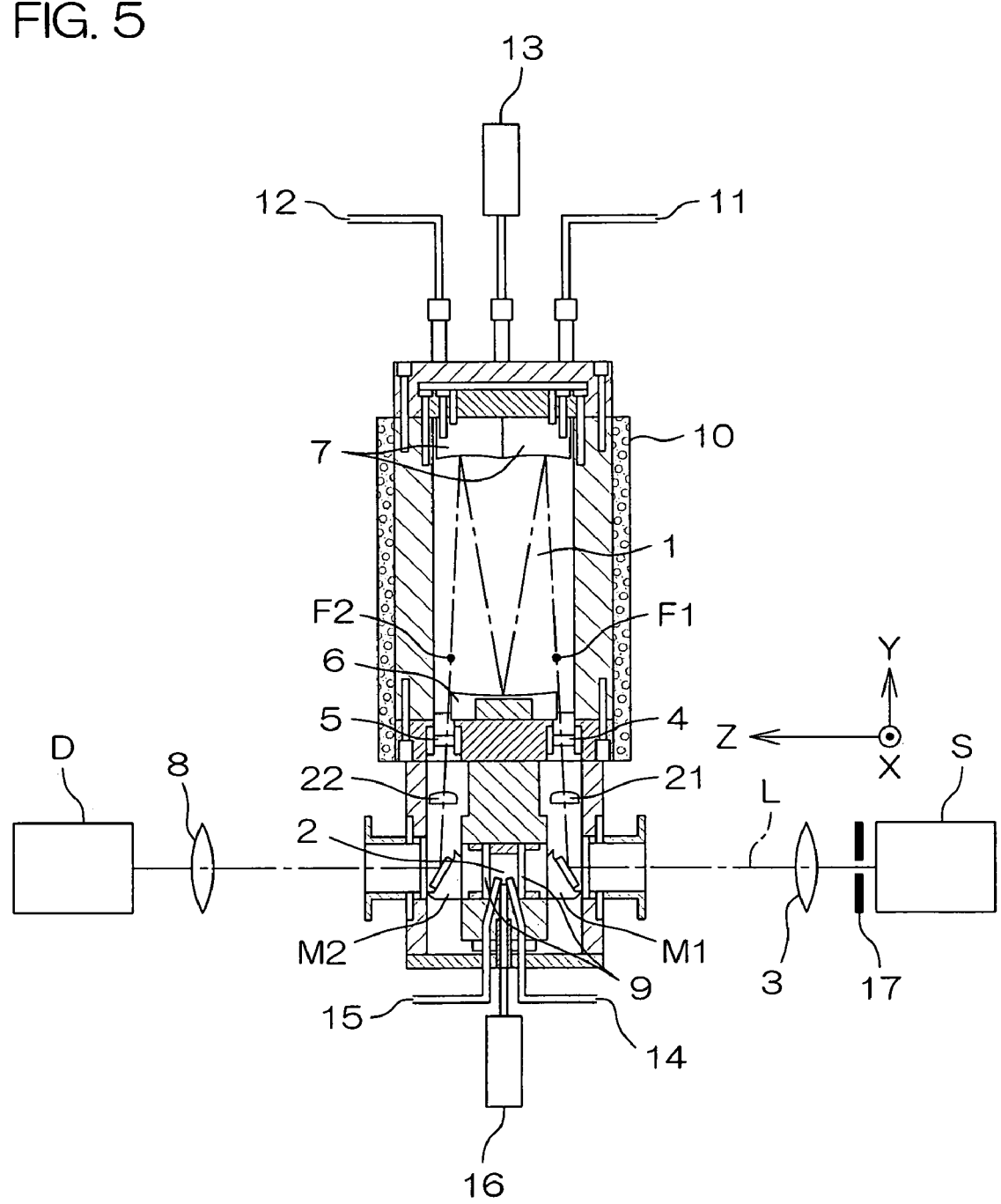
FIG. 5 is a sectional view of an optical cell measurement apparatus in which bifocal lenses are disposed between movable mirrors M1, M2 and gas cell windows according to another embodiment of the present invention.

While the embodiment of the present invention has thus been described, the invention is not limited to this embodiment. Although the bifocal lenses are respectively attached to the movable mirrors in the embodiment described above, the bifocal lenses may be provided separately from the movable mirrors. For example, the bifocal lenses 21, 22 may be respectively disposed in spaces between the movable mirrors M1, M2 and the gas cell windows 4, 5 as shown in FIG. 5. Though not shown, the bifocal lenses may be respectively provided between the light source S and the movable mirror M1 and between the movable mirror M2 and the sensor D.

Alternatively, the surfaces of the movable mirrors M1, M2 may be curved to be imparted with a bifocal property without the provision of the bifocal lenses. In this case, the surfaces of the movable mirrors M1, M2 may be processed so as to have different curvature radii as measured in the two directions. Further, reflective thin films may be formed on surfaces of the respective bifocal lenses by vapor deposition or the like, so that the bifocal lenses per se can serve as mirrors. Other various modifications may be made within the scope of the present invention.

The disclosure of Japanese patent application No. 2004-180256, filed Jun. 17, 2004, is incorporated herein by reference.

The invention claimed is:

1. An optical cell measurement apparatus for measuring a spectrum of a substance present in a gas cell, the apparatus comprising:
   a light source which emits light having a predetermined wavelength range;
   a first mirror which reflects the light emitted from the light source;
   a long light path gas cell to which the light reflected on the first mirror is introduced;
   a second mirror which reflects light outputted from the long light path gas cell;
   a sensor which detects the light reflected on the second mirror; and
   a bifocal optical element mounted on each of the first mirror and on the second mirror and each disposed in a light path extending from the light source to the sensor, each element having a bifocal property with different focal lengths as measured in two directions perpendicular to the light path.

2. An optical cell measurement apparatus as set forth in claim 1, further comprising:
   movement means which moves the first mirror and the second mirror away from the light path between the light source and the sensor; and
   a short light path gas cell disposed between the light source and the sensor in the light path from which the first mirror and the second mirror are retracted.

3. An optical cell measurement apparatus for measuring a spectrum of a substance present in a gas cell, the apparatus comprising:
   a light source which emits light having a predetermined wavelength range;
   a first mirror which reflects the light emitted from the light source;
   a long light path gas cell to which the light reflected on the first mirror is introduced;
   a second mirror which reflects light outputted from the long light path gas cell; and
   a sensor which detects the light reflected on the second mirror;
   wherein the first mirror and the second mirror each have a bifocal property with different focal lengths as measured in two directions perpendicular to a light path extending from the light source to the sensor.

4. An optical cell measurement apparatus as set forth in claim 3, further comprising:
   movement means which moves the first mirror and the second mirror away from the light path between the light source and the sensor; and
   a short light path gas cell disposed between the light source and the sensor in the light path from which the first mirror and the second mirror are retracted.

* * * * *